(12) United States Patent
Gandhi

(10) Patent No.: US 8,835,640 B1
(45) Date of Patent: Sep. 16, 2014

(54) NICOTINE DERIVATIVES

(71) Applicant: Paresh T. Gandhi, Totowa, NJ (US)

(72) Inventor: Paresh T. Gandhi, Totowa, NJ (US)

(*) Notice: Subject to any disclaimer, the term of this patent is extended or adjusted under 35 U.S.C. 154(b) by 0 days.

(21) Appl. No.: 14/120,260

(22) Filed: May 14, 2014

Related U.S. Application Data

(63) Continuation-in-part of application No. 13/694,205, filed on Nov. 7, 2012, now Pat. No. 8,754,228.

(60) Provisional application No. 61/629,387, filed on Nov. 16, 2011, provisional application No. 61/690,461, filed on Jun. 24, 2012.

(51) Int. Cl.
 *C07D 401/00* (2006.01)
 *C07D 409/14* (2006.01)
 *C07D 401/06* (2006.01)

(52) U.S. Cl.
 CPC ............ *C07D 401/06* (2013.01); *C07D 409/14* (2013.01)
 USPC ..................................... 546/278.4

(58) Field of Classification Search
 CPC ........................ C07D 401/06; C07D 409/14
 USPC ...................................... 546/278.4
 See application file for complete search history.

(56) References Cited

U.S. PATENT DOCUMENTS 8,754,228 B2 * 6/2014 Gandhi ................... 546/278.4

* cited by examiner

*Primary Examiner* — Nizal Chandrakumar
(74) *Attorney, Agent, or Firm* — Ralph T. Lilore

(57) ABSTRACT

Described are novel nicotine derivatives represented by general formulas (I) and (III), and salts thereof, and herbicide & pharmaceutical compositions containing the same as the active ingredient. The compound and salts thereof can control annual or perennial weed growing on the land where various crops such as rice plant, wheat, cotton and corn grow for a wide period ranging from the pre-emergence to growth in a remarkably small dose. The compounds and salts thereof can be useful as an anti-microbial and anti-fungal agents and also for the treatment of blood pressure, skeletal muscle, attention deficit disorder, mental disorders, schizophrenia, Alzheimer disease, Parkinson's disease and depression. Also described is the preparation of the nicotine derivatives having formula (I) and (III).

5 Claims, No Drawings

NICOTINE DERIVATIVES

CROSS REFERENCE TO RELATED APPLICATIONS

This application is a continuation-in-part of co-pending U.S. application Ser. No. 13/694,205 filed Nov. 7, 2012 which claims the benefit of U.S. Provisional Application No. 61/629,387 filed Nov. 16, 2011 and U.S. Provisional Application No. 61/690,461 filed Jun. 27, 2012.

STATEMENT REGARDING FEDERALLY SPONSORED RESEARCH OR DEVELOPMENT (Not Applicable)

REFERENCE TO A SEQUENCE LISTING A TABLE, OR A COMPUTER PROGRAM LISTING APPENDIX SUBMITTED ON A COMPACT DISC (SEE 37 CFR 1.52(e)(5)

(Not Applicable)

FIELD OF THE INVENTION

The present invention relates to novel nicotine derivatives represented by general formula (I), salts thereof, and compositions containing the same as an active ingredient. The compounds and salts thereof can control annual or perennial weed growing on the land where various crops such as rice plant, wheat, cotton and corn grow for a wide period ranging from the pre-emergence to growth in a remarkably small dose. The compound and salts thereof can be useful as an anti-microbial & anti-fungal agent, for the treatment of blood pressure, skeletal muscle, attention deficit disorder, mental disorders, schizophrenia, Alzheimer's disease & depression. The present invention also relates to the preparation of novel nicotine derivatives (formula (I).)

Nicotine is a well-known ingredient of smoking tobacco and is known to have deleterious effects when smoked, not the least of which is its addictive nature. Nicotine has one or more of insecticidal, pesticidal, anti-microbial, anti-fungal, and anti-depressant activities. It is believed that the addictive nature of nicotine is its ability to bind nicotine receptors in the body.

The invention thus relates to compounds which have some or all of the desirable effects of nicotine and lack the full intensity of the undesirable effects thereof. That is, an object of the invention is to provide bulky analogues of nicotine which are too large to bind to the nicotine receptors, yet retain at least to some extent, the desirable properties mentioned above.

BACKGROUND OF THE INVENTION

It is already known that nicotine derivatives have herbicidal activities. For example, nicotine acid derivatives represented by the formula;

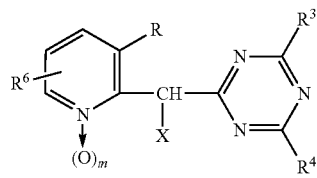

(Published Specification WO91/10653), heterocyclic derivatives represented by the formula

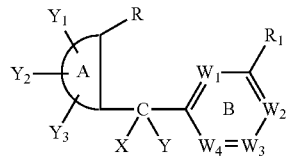

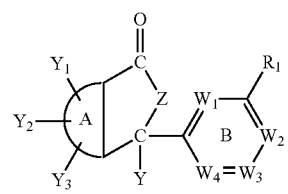

(Published Specification EPO461079) and nicotine acid derivative represented by the formula

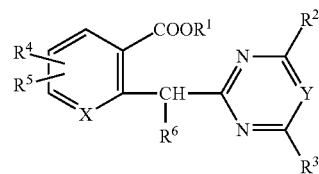

(Published Specification DE4026177) are known to have herbicidal activities.

U.S. Pat. No. 5,877,120 discloses the nicotine acid derivative having herbicidal activity, which is represented by the following formula;

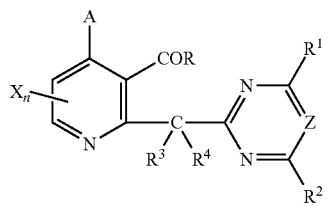

A number of other herbicides have been developed and contributed to labor saving in farm work and to the improvement of the productivity. However, in their practical use, such herbicides also have various problems with respect to the herbicidal effects and the safety to crop plants.

Especially, in cultivation of barley and wheat, few herbicides can control gramineous weeds congeneric to barley and wheat, such as water foxtail, black grass and annual blue grass over a broad period of time from the pre-emergence season to the growing season of the weeds. Further, few herbicides have a broad selectivity between these herbicides and barley or wheat.

The production of agricultural and horticultural crops and the like is still badly damaged by insect pests and the like, and the development of a novel agricultural and horticultural chemical, in particular, agricultural and horticultural insecticide is desired because of, for example, the appearance of insect pests resistant to existing chemicals. In addition, because of the increased population of aged farmers, and the like, various labor-saving application methods are desired and the development of an agricultural and horticultural chemical having properties suitable for the application methods is desired.

Further, the researchers have been talking about nicotine-related drugs for decades, but none are on the market yet. Part of the problem is reputation. Some have suggested that nicotine drugs be termed "cholinergic-channel modulators" to avoid the stigma.

"Nicotine is a pretty promiscuous drug," Dr. Newhouse explains. "It hits a lot of things at once. But for effective medications, we want to target specific receptor subtypes." Another obstacle is that nicotine-related compounds often have a fairly narrow therapeutic index: There isn't much difference between a dose that's helpful and one that's toxic. That isn't insurmountable, but it slows down clinical development.

Finally, the possibility that nicotine has angiogenic properties may put a damper on the research. In a review article on nicotine and angiogenesis published in 2004 in the Annals of Medicine, researchers John P. Cooke and Haim Bitterman said there was little reason to be worried about short-term use. In their opinion, nicotine gums and patches are safe and effective when "used as directed." But they called on scientists investigating the therapeutic potential of nicotine-like drugs to take the "potent angiogenic effects of nicotine" into account. Dr. Newhouse says the angiogenesis evidence comes largely from animal studies, so it doesn't necessarily apply to humans. He also points to the good safety record of the patch and other nicotine replacements, while noting that there has been some legitimate concern about the development of insulin resistance.

In a 2004 Psychopharmacology article, Dr. Newhouse and Alexandra Potter, Ph.D., reported that the high smoking rate among adolescents and adults with ADHD could be explained by their discovery that nicotine improves aspects of their mental functioning. Potter is recruiting people for two ADHD trials—one involving nicotine and the other a drug called mecamylamine, which blocks certain nicotine receptors.

An especially promising area of research involves cognitive impairments that are a precursor to Alzheimer's disease. In 2004, Duke University researchers published a small study on the effect of the nicotine patch in people with such impairments. They reported significant improvement in decision-making ability and attention (but not motor function or memory) in 11 subjects. Those results led to a larger study funded by the National Institute on Aging.

Rowland NE et. al. (Psychopharmacology (Berl). 2008-Sep.; 199(4):605-13) discloses that Nicotine analogs with alpha4beta2 nAChR partial agonist and antagonist efficacies can inhibit self-administration and may be considered as prototypical smoking-cessation agents.

Charles S. Pavia (Journal of Med. Microbiol. Vol 49 (2000), 674-675) discloses that of nicotine has ability to limit or interfere with growth of selected micro-organism was a significant finding.

Narang, Rakesh et. al. discloses that nicotine acid hydrazides derivative has antimycobacterial, antiviral, antibacterial and antifungal activities (Letters in Drug Design & Discovery, Volume 8, Number 8, October 2011, pp. 733-749 (17)).

The present inventor has conducted an extensive research on nicotine derivatives with the object of developing compounds which are not phytotoxic to valuable crop plants and have excellent herbicidal activities and also having good anti microbiological, anti-fungal activity.

The present inventor surprisingly found out the nicotine derivatives, which have good therapeutic effect and useful as medicament for the treatment of blood pressure, skeletal muscle, attention deficit disorder, mental disorder, schizophrenia, Alzheimer disease & depression.

SUMMARY OF THE INVENTION

In one embodiment, the present invention provides novel nicotine derivative of general formula (I) or salt thereof,

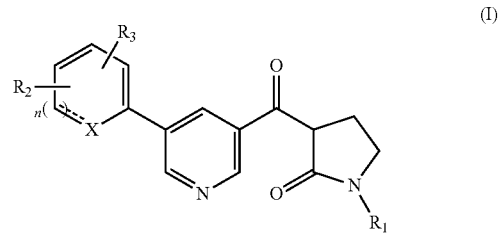

wherein:
X is CH, N or S;
n is 0 or 1;
$R_1$ is hydrogen, alkyl, acyl, halogen, alkoxy, aldehyde, hydroxy, cyano, nitro, amino, aryl, heteroaryl or heterocyclyl;
$R_2$ is hydrogen, acyl, alkyl, halogen, alkoxy, aldehyde, hydroxy, cyano, nitro, amino, aryl, heteroaryl or heterocyclyl.
$R_3$ is hydrogen, acyl, alkyl, halogen, alkoxy, aldehyde, hydroxy, cyano, nitro, amino, aryl, heteroaryl or heterocyclyl and wherein
$R_2$ and $R_3$ may be joined together to form a cycylic ring such as aryl, heteroaryl or heterocyclic.

In another embodiment, the present invention pertains to the nicotine acid derivatives set forth in formula (III) below and the salts thereof.

In another embodiment, the present invention includes synthetic intermediates that are useful in preparing the nicotine derivative of formula (I) and formula (III) and processes for preparing such intermediates.

In another embodiment, the present invention relates to the use of nicotine derivatives of formula (I) and (III) as herbicides, anti microbial agents, anti fungal agents and gents for the treatment of blood pressure, skeletal muscle, attention deficit disorder, mental disorder, schizophrenia, Alzheimer disease, Parkinson's disease and depression.

In another embodiment, the present invention relates to pharmaceutical compositions comprising a nicotine derivative of formula (I) or (III) as an active ingredient in a pharmaceutically effective amount, optionally in admixture with diluents, adjuvants and carriers.

Another embodiment of the present invention is a method for preparation of a compound of formula (I) or formula (III) as herein described. With regard to the compounds of the invention named herein, it should be noted that the letters (a)

through (j) and (4k) through 4y) appearing after the name of the compound are not part of the chemical name.

DETAILED DESCRIPTION OF THE INVENTION

In one embodiment, the present invention provides novel compounds of general formula (I)

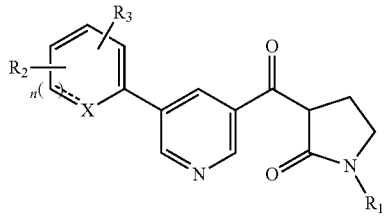

(I)

their salts, wherein $R_1$, $R_2$, $R_3$, X & n are as defined above.

A family of specific compounds of particular interest within the above formula (I) comprises compounds and salts thereof as follows:

3-(5-(5-acetylthiophen-2-yl)nicotinoyl)-1-methylpyrrolidin-2-one;
3-(5-(4-fluorophenyl)nicotinoyl)-1-methylpyrrolidin-2-one;
3-(5-(1-methyl-2-oxopyrrolidine-3-carbonyl)pyridin-3-yl) benzaldehyde;
1-methyl-3-(5-m-tolylnicotinoyl)pyrrolidin-2-one;
3-(5-(4-chlorophenyl)nicotinoyl)-1-methylpyrrolidin-2-one;
4-(5-(1-methyl-2-oxopyrrolidine-3-carbonyl)pyridin-3-yl) benzaldehyde;
3-(5-(3-methoxyphenyl)nicotinoyl)-1-methylpyrrolidin-2-one;
3-(5-(4-methoxyphenyl)nicotinoyl)-1-methylpyrrolidin-2-one;
1-methyl-3-(5-p-tolylnicotinoyl)pyrrolidin-2-one;
1-methyl-3-(5-phenylnicotinoyl)pyrrolidin-2-one;
3-(5-(3-fluorophenyl)nicotinoyl)-1-methylpyrrolidin-2-one;
1-methyl-3-(5-(3-nitrophenyl)nicotinoyl)pyrrolidin-2-one;
3-(5-(2-methoxyphenyl)nicotinoyl)-1-methylpyrrolidin-2-one;
1-methyl-3-(5-o-tolylnicotinoyl)pyrrolidin-2-one;
3-(5-(3,5-dichlorophenyl)nicotinoyl)-1-methylpyrrolidin-2-one;
1-methyl-3-(5-(naphthalen-1-yl)nicotinoyl)pyrrolidin-2-one;
3-(5-(3-acetylphenyl)nicotinoyl)-1-methylpyrrolidin-2-one;
3-(5-cyclopropylnicotinoyl)-1-methylpyrrolidin-2-one;
1-methyl-3-(5-(naphthalen-2-yl)nicotinoyl)pyrrolidin-2-one;
4-(5-(1-methyl-2-oxopyrrolidine-3-carbonyl)pyridin-3-yl) phenyl acetate;
3-(5-(1-methyl-2-oxopyrrolidine-3-carbonyl)pyridin-3-yl) benzaldehyde;
3-(5-(3-hydroxyphenyl)nicotinoyl)-1-methylpyrrolidin-2-one;
3-(5-(2-chlorophenyl)nicotinoyl)-1-methylpyrrolidin-2-one;
3-(5-(3-aminophenyl)nicotinoyl)-1-methylpyrrolidin-2-one.

In another embodiment, the present invention provides novel nicotine derivative of general formula III or salts thereof,

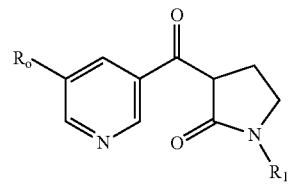

III wherein: $R_o$ is straight chain alkyl, branched chain alkyl, or cyclic alkyl or the group

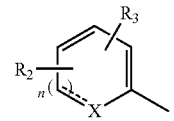

and n, X, $R_1$, $R_2$ and $R_3$ are as previously described herein.

A specific compound of particular interest within general formula (III) is 3-(5-butylnicotinoyl)-1-methylpyrrolidin-2-one.

DEFINITIONS

The following definitions apply to the terms as used throughout this specification, unless otherwise limited in specific instances:

The term "derivative" employed herein refers to any compound encompassed by the generic formula disclosed herein. The derivative described herein may contain one or more double bonds and therefore, may exist as isomers, stereoisomers, such as geometric isomers, E and Z isomers, and may possess asymmetric carbon atoms (optical centres) and therefore may exist as enantiomers, diastereoisomers. The derivative may also exist in several tautomeric forms including the enol form, the keto form and mixtures thereof. Accordingly, the chemical structures described herein encompass all possible tautomeric forms of the illustrated compounds. The nictonic acid derivative described also include isotopically labeled compounds where one or more atoms have an atomic mass different from the atomic mass conventionally found in nature.

The term "substituted", as used herein, includes mono- and poly-substitution by a named substituent to the extent such single and multiple substitution (including multiple substitution at the same site) is chemically allowed and which means that any one or more hydrogens on the designated atom is replaced with a selection from the indicated group, provided that the designated atom's normal valence is not exceeded, and that the substitution results in a stable compound, for example, when a substituent is keto, then the two hydrogens on the atom are replaced.

The use of the terms "a" and "an" and "the" and similar referents in the context of describing the invention (especially in the context of the following claims) are to be construed to cover both the singular and the plural, unless otherwise indicated herein or clearly contradicted by context.

The term "salt", as used herein refers to a salt of a compound, which possesses the desired activity of the parent compound.

As used herein, "alkyl" means a saturated hydrocarbon, including, straight or branched saturated hydrocarbon chains such as methyl ethyl, propyl, 1-methylethyl, butyl, 1-methylpropyl, 1,1-dimethylethyl, hexyl, octyl, decyl, dodecyl, stearyl, and saturated hydrocarbon rings, such as cyclopropyl, cyclohexyl and cyclooctyl, etc.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

In another embodiment, present invention provides the process for preparing the nicotine acid derivative of formula (I).

The following reaction schemes are given to disclose the synthesis of the nicotine acid derivative of formula (I) and other compounds within formula III according to the present invention. Accordingly, compounds of the present invention may be prepared as described in the schemes below using the appropriate variations in reagents required by the structure of the final compound.

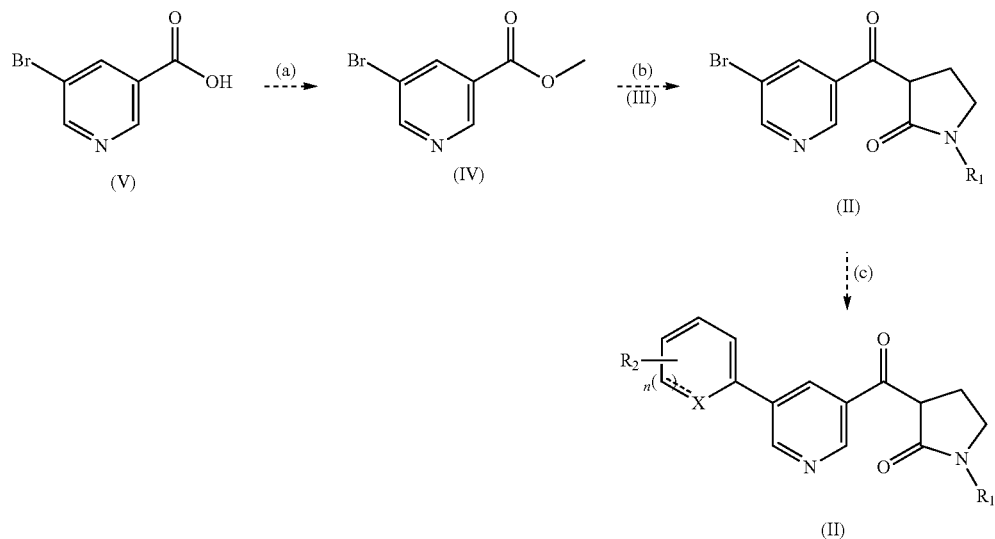

The term "acyl", as used herein, represents a group of formula —C(=O)$R_b$, wherein $R_b$ is $C_{1-6}$ alkyl, $C_{1-6}$-alkyl hydroxy, $C_{1-6}$-alkyl amino or $C_{1-6}$-alkyl aminocarbonyl, as defined herein.

The term "aldehyde" as used herein, means a group represented by —CHO.

As used herein, a "halo" or "halogen" substituent is a monovalent halogen radical chosen from chloro, bromo, iodo or fluoro.

The term "aryl" refers to an aromatic group for example, which is a 5 to 10 membered monocyclic or bicyclic carbon-containing ring system, which may be unsubstituted or substituted.

The term "heteroaryl" refers to an aromatic group for example, which is a 3 to 10 membered monocyclic or bicyclic ring system, which has at least one heteroatom, which may be unsubstituted or substituted. The term "heteroatom" as used herein includes oxygen, sulfur and nitrogen.

The term "heterocyclyl" refers to a fully saturated or unsaturated nonaromatic cyclic group, for example, which is a 3 to 10 membered monocyclic or bicyclic ring system, which has at least one heteroatom, which may be unsubstituted or substituted. The term "heteroatom" as used herein includes oxygen, sulfur and nitrogen.

Throughout this specification and the appended claims it is to be understood that the words "comprise" and "include" and variations such as "comprises", "comprising", "includes", "including" are to be interpreted inclusively, unless the context requires otherwise. That is, the use of these words may imply the inclusion of an element or elements not specifically recited.

Step-(a):
5-bromonicotine acid (10 g, 49.76 mmol) is alkylated with alkylating agent like methanol in the presence of concentrated sulfuric acid at 0° C. under nitrogen atmosphere to obtain alkyl-5-bromonicotinate.

Step-(b):
Alkyl-5-bromonicotinate is reacted with pyrrolidine derivative of formula (VII) represented by below general formula

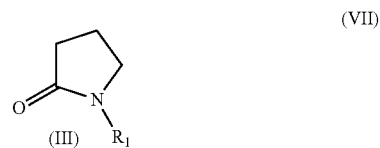

in suitable solvent like toluene, dimethylformamide, dichloromethane, xylene, dimethylsulofixde in the presence of base like sodium hydroxide, sodium hydroxide, sodium carbonate, etc at reflux temperature.

Step-(c):
A compound of formula (II) is reacted with boronic acid derivative of formula (VI)

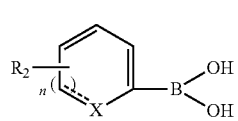

in the presence of catalyst like 1,1'-bis(diphenylphosphino) ferrocene]dichloro palladium(II) in suitable solvent like suitable solvent like toluene, dimethylformamide, 1,4-dioxane, dichloromethane, xylene, dimethylsulofixde or mixture thereof in the presence of base like sodium hydroxide, sodium hydroxide, sodium carbonate under nitrogen atmosphere.

The herbicide of the present invention comprises a nicotine acid derivative of the general formula (I) as an active ingredient.

For the compound of the present invention to be used as a herbicide, the compound of the present invention may be used by itself. However, it may be used in the form of a formulation such as a dust, a wettable powder, an emulsifiable concentrate, a microgranule or a granule by blending it with a carrier, a surfactant, a dispersant or an adjuvant which is commonly used for formulations.

The carrier to be used for such formulations, may, for example, be a solid carrier such as zeeklite, talc, bentonite, clay, kaolin, diatomaceous earth, white carbon, vermiculite, calcium carbonate, slaked lime, siliceous sand, ammonium sulfate or urea, or a liquid carrier such as isopropyl alcohol, xylene, cyclohexanone or methylnaphthalene.

As the surfactant and dispersant, a metal salt of alkylbenzenesulfonic acid, a metal salt of dinaphthylmethanedisulfonic acid, a salt of an alcohol sulfuric acid ester, an alkylaryl sulfonate, a lignin sulfonate, a polyoxyethylene glycol ether, a polyoxyethylene alkyl aryl ether or a polyoxyethylene sorbitol monoalkylate may, for example, be mentioned. The adjuvant may, for example, be carboxymethyl cellulose, polyethylene glycol or gum arabic. In practical use, the herbicide may be diluted to a suitable concentration before application, or may be directly applied.

The herbicide of the present invention may be used for application to foliage, soil or water surface. The blending proportion of the active ingredient is suitably selected as the case requires. However, in the case of a dust or a granule, the proportion of the active ingredient is selected suitably within a range of from 0.01 to 10% by weight, preferably from 0.05 to 5% by weight. In the case of an emulsifiable concentrate or a wettable powder, the proportion is selected suitably within a range of from 1 to 50% by weight, preferably from 5 to 30% by weight.

The dose of the herbicide of the present invention varies depending upon the type of the compound, the weeds to be controlled, the germination tendency, the environmental conditions and the type of the formulation to be used. However, in the case of a dust or a granule which is used by itself, the dose of the active ingredient is selected suitably within a range of from 0.1 g to 5 kg, preferably from 1 g to 1 kg, per 10 ares. In the case of an emulsifiable concentrate or a wettable powder which is used in a liquid state, the dose of the active ingredient is selected suitably within a range of from 0.1 to 50,000 ppm, preferably from 10 to 10,000 ppm.

Further, the compound of the present invention may be used in combination with an insecticide, a fungicide, another herbicide, a plant growth controlling agent, a fertilizer or the like, as the case requires.

Now, the formulation method will be described with reference to typical Formulation Examples. The compounds, types of the additives and blending ratios are not limited to such specific Examples and may be changed within wide ranges. In the following description, "parts" means "parts by weight".

In another embodiment of the invention there is provided a pharmaceutical composition comprising a therapeutically effective amount of one or more of a compound of formula (I) or formula (III). While it is possible to administer therapeutically effective quantity of compounds of formula (I) either individually or in combination, directly without any formulation, it is common practice to administer the compounds in the form of pharmaceutical dosage forms comprising pharmaceutically acceptable excipient(s) and at least one active ingredient. These dosage forms may be administered by a variety of routes including oral, topical, transdermal, subcutaneous, intramuscular, intravenous, intranasal, pulmonary etc. Oral compositions may be in the form of solid or liquid dosage form. Solid dosage form may comprise pellets, pouches, sachets or discrete units such as tablets, multi-particulate units, capsules (soft & hard gelatin) etc. Liquid dosage forms may be in the form of elixirs, suspensions, emulsions, solutions, syrups etc. Composition intended for oral use may be prepared according to any method known in the art for the manufacture of the composition and such pharmaceutical compositions may contain in addition to active ingredients, excipients such as diluents, disintegrating agents, binders, solubilizers, lubricants, glidants, surfactants, suspending agents, emulsifiers, chelating agents, stabilizers, flavours, sweeteners, colours etc. Some example of suitable excipients include lactose, cellulose and its derivatives such as microcrystalline cellulose, methylcellulose, hydroxy propyl methyl cellulose & ethylcellylose, dicalcium phosphate, mannitol, starch, gelatin, polyvinyl pyrolidone, various gums like acacia, tragacanth, xanthan, alginates & its derivatives, sorbitol, dextrose, xylitol, magnesium Stearate, talc, colloidal silicon dioxide, mineral oil, glyceryl mono stearate, glyceryl behenate, sodium starch glycolate, cross povidone, crosslinked carboxymethylcellulose, various emulsifiers such as polyethylene glycol, sorbitol, fatty acid esters, polyethylene glycol alkylethers, sugar esters, polyoxyethylene polyoxypropyl block copolymers, polyethoxylated fatty acid monoesters, diesters and mixtures thereof.

Sterile compositions for injection can be formulated according to conventional pharmaceutical practice by dissolving or suspending the active substance in a vehicle such as water for injection, N-Methyl-2-Pyrrolidone, propylene glycol and other glycols, alcohols, a naturally occurring vegetable oil like sesame oil, coconut oil, peanut oil, cotton seed oil or a synthetic fatty vehicle like ethyl oleate or the like. Buffers, antioxidants, preservatives, complexing agents like cellulose derivatives, peptides, polypeptides and cyclodextrins and the like can be incorporated as required.

The dosage form can have a slow, delayed or controlled release of active ingredients in addition to immediate release dosage forms.

The amount of active ingredient which is required to achieve a therapeutic effect will, of course, vary with the particular compound, the route of administration, the subject under treatment, and the particular disorder or disease being treated. The compounds of the invention may be administered orally or parenterally at a dose ranging from 0.001 to 1500 mg/kg per day, preferably from 0.01 to 1500 mg/kg per day, more preferably from 0.1 to 1500 mg/kg per day, most preferably from 0.1 to 500 mg/kg per day. The dose range for adult humans is generally from 5 mg to 35 g per day and preferably 5 mg to 2 g per day.

Tablets or other dosage forms of presentation provided in discrete units may conveniently contain an amount of compound of the invention which is effective at such dosage or as a multiple of the same, for example units containing 1 mg to 1500 mg.

The processes described in the present invention were demonstrated in examples illustrated below. These examples are provided as illustration only and therefore should not be construed as limitation of the scope of the invention.

EXAMPLES

Example-1

Preparation of methyl 5-bromonicotinate

A solution of 5-bromonicotine acid (10 g, 49.76 mmol) in 200 ml of methanol was cooled to 0° C. under nitrogen atmosphere and was added conc.H2SO4 (2.4 ml, 49.76 mmol) slowly drop wise. And slowly heated to reflux and continued for 15 h, after completion of the reaction volatiles were removed under reduced pressure. The resulting solid was dissolved in ethyl acetate (200 ml) and washed with saturated sodium bicarbonate solution (2×50 ml), the combined organic layer was dried over with sodium sulfate, filtered and evaporated under reduced pressure to obtain methyl 5-bromonicotinate 2 as an off white solid (9.1 g, 85.1% yield).

1HNMR (500 MHz, CDCl3): δ ppm: 9.12 (s, 1H), 8.84 (s, 1H), 8.43 (s, 1H), 3.96 (s, 3H); Mass (m/z): 216 (M+H)+, 218 (M+2H)+.

Example-2

Preparation of 3-(5-bromonicotinoyl)-1-methylpyrrolidin-2-one

A suspension of NaH (60% in oil, 1.84 g, 46 mmol) was washed with toluene (3×10 ml) under nitrogen atmosphere. The resulting slurry in 50 ml of toluene was refluxed for 30 minutes under nitrogen and to it was added slowly a toluene (25 ml) solution of methyl 5-bromonicotinate (5 g, 23.26 mmol) and 1-methyl-2-pyrrolidone (4.58 g, 46.5 mmol) for 45 minutes. Then the reaction mixture was refluxed for 10 h. After completion of the reaction cooled to room temperature and added 10 ml of saturated ammonium chloride. The separated organic layer was dried over with sodium sulfate, filtered and evaporated under reduced pressure to obtain crude residue which was purified by silica-gel column chromatography using EtOAc/hexane (60:40) as an eluent to afford an off white solid (1.6 g, 24.4% yield).

1HNMR (500 MHz, CDCl3): δ ppm: 9.21 (s, 1H), 8.84 (s, 1H), 8.54 (s, 1H), 4.38 (q, 1H), 3.58 (m, 1H), 3.43 (m, 1H), 2.86 (s, 3H), 2.72 (m, 1H), 2.25 (m, 1H); Mass (m/z): 216 (M+H)+, 218 (M+2H)+.

Example-3

Synthesis of Compound Number ARP100101, i.e., 3-(5-(5-acetylthiophen-2-yl)nicotinoyl)-1-methylpyrrolidin-2-one

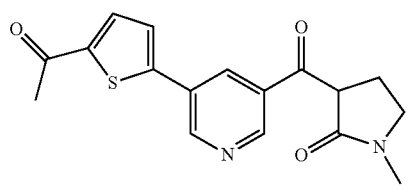 [SMILES: CC(=O)c1ccc(-c2cncc(C(=O)C3CCN(C)C3=O)c2)s1]

A mixture of 3-(5-bromonicotinoyl)-1-methylpyrrolidin-2-one 3 (1 equiv), 5-Acetyl-2-thiopheneboronic acid (1.2 equiv), 1,1'-bis(diphenylphosphino)ferrocene]dichloro palladium(II) complex with DCM (0.1 equiv) and 2M Na2CO3(4 equiv) in toluene/1,4-dioxane(4:1, 15 volumes) was degassed and filled with nitrogen. Then the reaction mixture was heated to 85° C. and maintained for 2 h. After completion of the reaction filtered through Celite bed and washed with ethyl acetate. The combined organic layer was dried over with anhydrous sodium sulfate, filtered and concentrated under reduced pressure to obtain crude residue which was purified by silica-gel column chromatography using 2% MeOH/DCM as an eluent to afford 50% yield of titled compound.

1HNMR (500 MHz, CDCl3): δ ppm: 9.27 (s, 1H), 9.06 (s, 1H), 8.66 (s, 1H), 7.61 (d, 1H), 7.19 (d, 1H), 4.46 (t, 1H), 3.60 (m, 1H), 3.41 (m, 1H), 2.87 (s, 3H), 2.78 (m, 1H), 2.58 (s, 3H), 2.26 (m, 1H); Mass (m/z): 329.2 (M+H)+

The following representative compounds of the present invention were prepared in analogus manner by following the synthetic routes as described above:

Example-4

Synthesis of Compound Number ARP100102, i.e., 3-(5-(4-fluorophenyl)nicotinoyl)-1-methylpyrrolidin-2-one

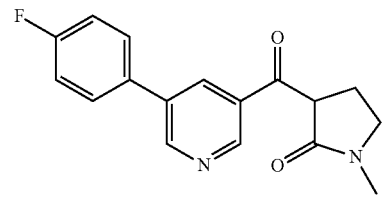 [SMILES: CN1CCC(C(=O)c2cncc(-c3ccc(F)cc3)c2)C1=O]

1HNMR (500 MHz, CDCl3): δ ppm: 9.26 (s, 1H), 8.97 (s, 1H), 8.60 (s, 1H), 7.7 (d, 1H), 7.46 (d, 1H), 4.45 (t, 1H), 3.60 (m, 1H), 3.42 (m, 1H), 2.86 (s, 3H), 2.78 (m, 1H), 2.58 (s, 3H), 2.24 (m, 1H); Mass (m/z): 299.2 (M+H)+.

Example-5

Synthesis of Compound Number ARP100103, i.e., 3-(5-(1-methyl-2-oxopyrrolidine-3-carbonyl)pyridin-3-yl)benzaldehyde

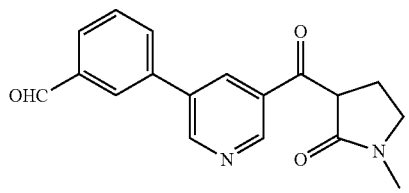 [SMILES: CN1CCC(C(=O)c2cncc(-c3cccc(C=O)c3)c2)C1=O]

1HNMR (500 MHz, CDCl3): δ ppm 10.11 (s, 1H), 9.05 (s, 1H), 8.68 (s, 1H), 8.15 (s, 1H), 7.94 (m, 2H), 7.69 (t, 1H), 4.51 (t, 1H), 3.61 (m, 1H), 3.42 (m, 1H), 2.88 (s, 3H), 2.78 (m, 1H), 2.58 (s, 3H), 2.28 (m, 1H); Mass (m/z): 309.2 (M+H)+.

Example-6

Synthesis of Compound Number ARP100104, i.e., 1-methyl-3-(5-m-tolylnicotinoyl)pyrrolidin-2-one

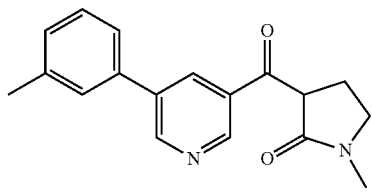 [SMILES: Cc1cccc(-c2cncc(C(=O)C3CCN(C)C3=O)c2)c1]

1HNMR (500 MHz, CDCl3): δ ppm: 9.26 (□□s, 1H), 9.00 (s, 1H), 8.60 (s, 1H), 7.38-7.42 (m, 3H), 7.22 (s, 1H), 4.49 (t, 1H), 3.61 (m, 1H), 3.44 (m, 1H), 2.88 (s, 3H), 2.74 (m, 1H), 2.44 (s, 3H), 2.28 (m, 1H); Mass (m/z): 295.2 (M+H)+.

Example-7

Synthesis of Compound Number ARP100105, i.e., 3-(5-(4-chlorophenyl)nicotinoyl)-1-methylpyrrolidin-2-one

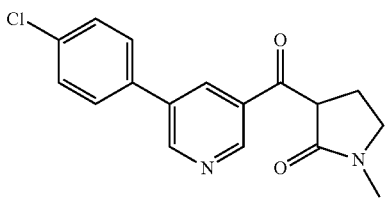 [SMILES: CN1CCC(C(=O)c2cncc(-c3ccc(Cl)cc3)c2)C1=O]

1HNMR (500 MHz, CDCl3): δ ppm: 9.15 (□□d, 2H), 8.64 (s, 1H), 7.87 (d, 2H), 7.61 (d, 1H), 4.90 (t, 1H), 3.40-3.43 (m, 2H), 2.74 (s, 3H), 2.21 (s, 2H); Mass (m/z): 315.2 (M+H)+.

Example-8

Synthesis of Compound Number ARP100106, i.e., 4-(5-(1-methyl-2-oxopyrrolidine-3-carbonyl)pyridin-3-yl)benzaldehyde

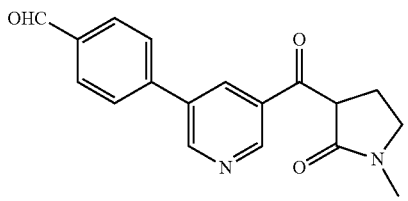 [SMILES: CN1CCC(C(=O)c2cncc(-c3ccc(C=O)cc3)c2)C1=O]

1HNMR (500 MHz, CDCl3): δ□ ppm: □10.09 (□□s, 1H), 9.34 (s, 1H), 9.06 (s, 1H), 8.71 (s, 1H), 8.03 (d, 2H), 7.84 (d, 2H), 4.50 (q, 1H), 3.63 (m, 1H), 3.47 (m, 1H), 2.89 (s, 3H), 2.80 (m, 1H), 2.30 (m, 1H); Mass (m/z): 309.2 (M+H)+.

Example-9

Synthesis of Compound Number ARP100107, i.e., 3-(5-(3-methoxyphenyl)nicotinoyl)-1-methylpyrrolidin-2-one

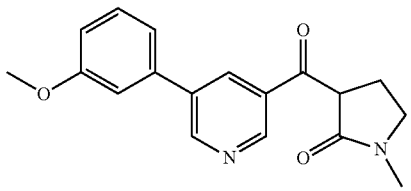 [SMILES: COc1cccc(-c2cncc(C(=O)C3CCN(C)C3=O)c2)c1]

1HNMR (500 MHz, CDCl3): δ ppm: □9.28 (□□s, 1H), 9.01 (s, 1H), 8.61 (s, 1H), 7.42 (t, 1H), 7.26 (s, 1H), 7.24 (d, 1H), 6.99 (d, 1H), 4.50 (t, 1H), 3.88 (s, 3H), 3.62 (m, 1H), 3.45 (m, 1H), 2.88 (s, 3H), 2.76 (m, 1H), 2.30 (m, 1H); Mass (m/z): 311.2 (M+H)+.

Example-10

Synthesis of Compound Number ARP100108, i.e., 3-(5-(4-methoxyphenyl)nicotinoyl)-1-methylpyrrolidin-2-one

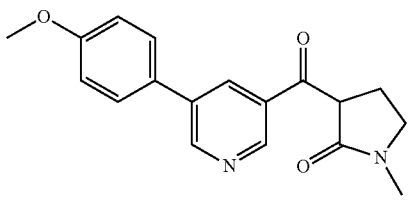 [SMILES: COc1ccc(-c2cncc(C(=O)C3CCN(C)C3=O)c2)cc1]

1HNMR (500 MHz, CDCl3): δ□ ppm: □9.22 (□□s, 1H), 8.98 (s, 1H), 8.59 (s, 1H), 7.59 (d, 2H), 7.03 (d, 2H), 4.48 (t, 1H), 3.87 (s, 3H), 3.62 (m, 1H), 3.42 (m, 1H), 2.88 (s, 3H), 2.78 (m, 1H), 2.26 (m, 1H); Mass (m/z): 311.2 (M+H)+.

Example-11

Synthesis of Compound Number ARP100109, i.e., 1-methyl-3-(5-p-tolylnicotinoyl)pyrrolidin-2-one

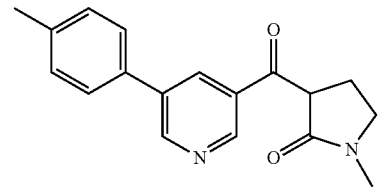 [SMILES: Cc1ccc(-c2cncc(C(=O)C3CCN(C)C3=O)c2)cc1]

1HNMR (500 MHz, CDCl3): δ ppm: □9.25 (□□s, 1H), 9.00 (s, 1H), 8.61 (s, 1H), 7.53 (d, 2H), 7.31 (d, 2H), 4.5 (t, 1H), 3.63 (m, 1H), 3.46 (m, 1H), 2.89 (s, 3H), 2.77 (m, 1H), 2.42 (s, 3H), 2.28 (m, 1H); Mass (m/z): 295.3 (M+H)+.

Example-12

Synthesis of Compound Number ARP100110 or ARP10010, i.e., 1-methyl-3-(5-phenylnicotinoyl)pyrrolidin-2-one

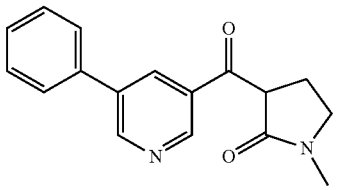 [SMILES: CN1CCC(C(=O)c2cncc(-c3ccccc3)c2)C1=O]

1HNMR (500 MHz, CDCl3): δ ppm: 9.28 (s, 1H), 9.02 (s, 1H), 8.64 (s, 1H), 7.65 (d, 2H), 7.42-7.52 (m, 3H), 4.51 (q, 1H), 3.63 (m, 1H), 3.45 (m, 1H), 2.89 (s, 3H), 2.76 (m, 1H), 2.30 (m, 1H); Mass (m/z): 281.2 (M+H)+.

Example-13

Synthesis of Compound Number ARP100111, i.e., 3-(5-(3-fluorophenyl)nicotinoyl)-1-methylpyrrolidin-2-one

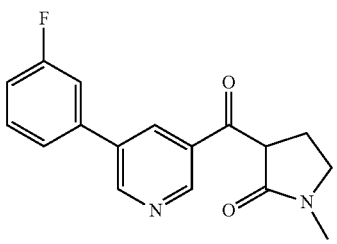 [SMILES: CN1CCC(C(=O)c2cncc(-c3cccc(F)c3)c2)C1=O]

¹HNMR (500 MHz, CDCl3): δ ppm: 9.29 (s, 1H), 8.96 (s, 1H), 8.61 (s, 1H), 7.46-7.25 (m, 3H), 7.12 (t, 1H), 4.42 (m, 1H), 3.60 (m, 1H), 3.44 (m, 1H), 2.87 (s, 3H), 2.78 (m, 1H), 2.26 (m, 1H); Mass (m/z): 299.3 (M+H)⁺

Example-14

Synthesis of Compound Number ARP100112, i.e., 1-methyl-3-(5-(3-nitrophenyl)nicotinoyl)pyrrolidin-2-one

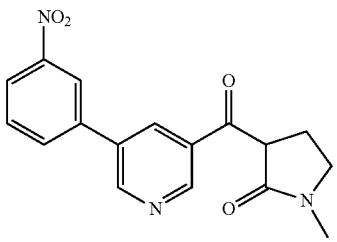 [SMILES: CN1CCC(C(=O)c2cncc(-c3cccc([N+](=O)[O-])c3)c2)C1=O]

¹HNMR (500 MHz, CDCl3): δ ppm: 9.35 (s, 1H), 9.05 (s, 1H), 8.68 (s, 1H), 8.50 (s, 1H), 8.30 (d, 1H), 7.96 (d, 1H), 3.61 (m, 1H), 3.42 (m, 1H), 3.35 (m, 1H), 2.87 (s, 3H), 2.28 (m, 1H); Mass (m/z): 326.3 (M+H)⁺.

Example-15

Synthesis of Compound Number ARP100113, i.e., 3-(5-(2-methoxyphenyl)nicotinoyl)-1-methylpyrrolidin-2-one

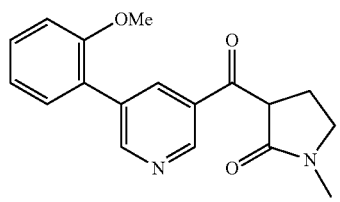 [SMILES: COc1ccccc1-c1cncc(C(=O)C2CCN(C)C2=O)c1]

¹HNMR (500 MHz, CDCl3): δ ppm: 9.23 (s, 1H), 8.95 (s, 1H), 8.55 (s, 1H), 7.25-7.36 (m, 2H), 7.05 (m, 2H), 4.47 (m, 1H), 3.82 (s, 3H), 3.60 (m, 1H), 3.42 (m, 1H), 2.87 (s, 3H), 2.70 (m, 1H), 2.15 (m, 1H); Mass (m/z): 311.3 (M+H)⁺.

Example-16

Synthesis of Compound Number ARP100114, i.e., 1-methyl-3-(5-o-tolylnicotinoyl)pyrrolidin-2-one

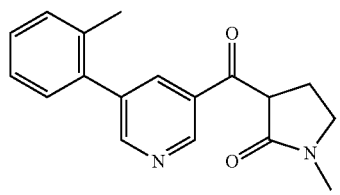 [SMILES: Cc1ccccc1-c1cncc(C(=O)C2CCN(C)C2=O)c1]

¹HNMR (500 MHz, CDCl3): δ ppm: 9.28 (s, 1H), 8.76 (s, 1H), 8.39 (s, 1H), 7.25-7.31 (m, 4H), 4.46 (q, 1H), 3.62 (m, 1H), 3.42 (m, 1H), 2.87 (s, 3H), 2.74 (m, 1H), 2.30 (s, 3H), 2.28 (m, 1H); Mass (m/z): 295.3 (M+H)⁺.

Example-17

Synthesis of Compound Number ARP100115, i.e., 3-(5-(3,5-dichlorophenyl)nicotinoyl)-1-methylpyrrolidin-2-one

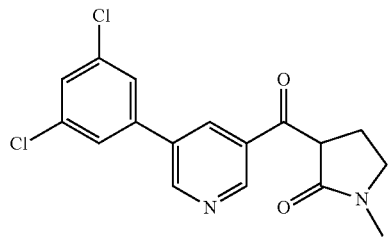 [SMILES: CN1CCC(C(=O)c2cncc(-c3cc(Cl)cc(Cl)c3)c2)C1=O]

¹HNMR (500 MHz, CDCl3): δ ppm: 9.32 (s, 1H), 8.95 (s, 1H), 8.56 (s, 1H), 7.42-7.50 (m, 3H), 4.45 (t, 1H), 3.60 (m, 1H), 3.44 (m, 1H), 2.90 (s, 3H), 2.76 (m, 1H), 2.26 (m, 1H); Mass (m/z): 349.1 (M+H)⁺.

Example-18

Synthesis of Compound Number ARP100116, i.e., 1-methyl-3-(5-(naphthalen-1-yl)nicotinoyl)pyrrolidin-2-one

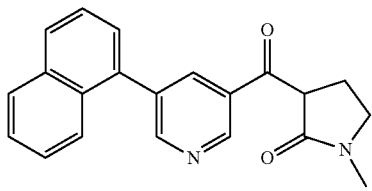 [SMILES: CN1CCC(C(=O)c2cncc(-c3cccc4ccccc34)c2)C1=O]

¹HNMR (500 MHz, CDCl3): δ ppm: 9.37 (s, 1H), 8.93 (s, 1H), 8.54 (s, 1H), 7.93 (d, 2H), 7.80 (d, 2H), 7.40-7.60 (m, 6H), 4.48 (t, 1H), 3.59 (m, 1H), 3.42 (m, 1H), 2.88 (s, 3H), 2.75 (m, 1H), 2.44 (m, 1H), Mass (m/z): 331.2 (M+H)⁺.

Example-19

Synthesis of Compound Number ARP100117, i.e., 3-(5-(3-acetylphenyl)nicotinoyl)-1-methylpyrrolidin-2-one

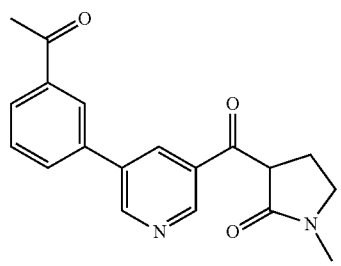 [SMILES: CC(=O)c1cccc(-c2cncc(C(=O)C3CCN(C)C3=O)c2)c1]

¹HNMR (500 MHz, CDCl3): δ ppm: 9.32 (s, 1H), 9.06 (s, 1H), 8.66 (s, 1H), 8.22 (s, 1H), 8.00 (d, 1H), 7.82 (d, 1H), 7.61 (t, 1H), 4.50 (m, 1H), 3.62 (m, 1H), 3.42 (m, 1H), 2.86 (s, 3H), 2.80 (s, 3H), 2.30 (m, 1H); Mass (m/z): 323.2 (M+H)⁺.

Example-20

Synthesis of Compound Number ARP100118, i.e., 3-(5-cyclopropylnicotinoyl)-1-methylpyrrolidin-2-one

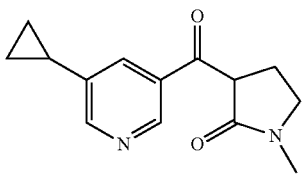 [SMILES: CN1CCC(C(=O)c2cncc(C3CC3)c2)C1=O]

¹HNMR (500 MHz, CDCl3): δ ppm: 9.06 (s, 1H), 8.58 (s, 1H), 7.98 (s, 1H), 4.40 (q, 1H), 3.60 (m, 1H), 3.42 (m, 1H), 2.85 (s, 3H), 2.72 (m, 1H), 2.28 (m, 1H); Mass (m/z): 245.1 (M+H)⁺.

Example-21

Synthesis of Compound Number ARP100119, i.e., 1-methyl-3-(5-(naphthalen-2-yl)nicotinoyl)pyrrolidin-2-one

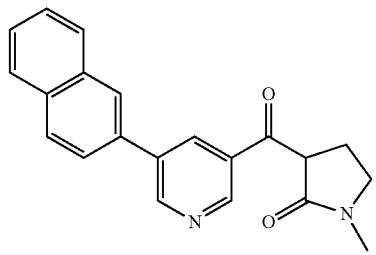 [SMILES: CN1CCC(C(=O)c2cncc(-c3ccc4ccccc4c3)c2)C1=O]

¹HNMR (500 MHz, CDCl3): δ ppm: 9.30 (s, 1H), 9.16 (s, 1H), 8.75 (s, 1H), 8.08 (s, 1H), 7.70-7.95 (m, 4H), 7.50 (d, 2H), 4.52 (q, 1H), 3.61 (m, 1H), 3.42 (m, 1H), 2.86 (s, 3H), 2.78 (m, 1H), 2.28 (m, 1H); Mass (m/z): 331.4 (M+H)⁺.

Example-22

Synthesis of Compound Number ARP100120, i.e., 4-(5-(1-methyl-2-oxopyrrolidine-3-carbonyl)pyridin-3-yl)phenyl acetate

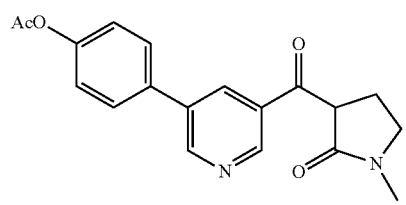 [SMILES: CC(=O)Oc1ccc(-c2cncc(C(=O)C3CCN(C)C3=O)c2)cc1]

¹HNMR (500 MHz, CDCl3): δ ppm: 9.31 (s, 1H), 9.04 (s, 1H), 8.67 (s, 1H), 8.08 (d, 2H), 7.75 (d, 1H), 4.49 (q, 1H), 3.62 (m, 1H), 3.44 (m, 1H), 2.88 (s, 3H), 2.80 (m, 1H), 2.42 (s, 3H), 2.26 (m, 1H); Mass (m/z): 323.3 (M+H)⁺.

Example-23

Synthesis of Compound Number ARP100121, i.e., 3-(5-(1-methyl-2-oxopyrrolidine-3-carbonyl)pyridin-3-yl)benzaldehyde

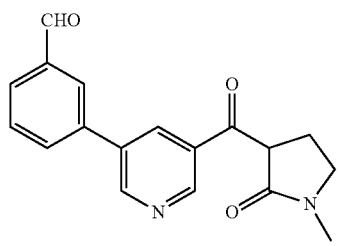 [SMILES: CN1CCC(C(=O)c2cncc(-c3cccc(C=O)c3)c2)C1=O]

¹HNMR (500 MHz, CDCl3): δ ppm: 10.11 (s, 1H), 9.32 (s, 1H), 9.06 (s, 1H), 8.67 (s, 1H), 8.14 (s, 1H), 7.94 (m, 2H), 7.68 (d, 1H) 4.49 (t, 1H), 3.61 (m, 1H), 3.44 (m, 1H), 2.86 (s, 3H), 2.76 (m, 1H), 2.44 (s, 3H), 2.28 (m, 1H); Mass (m/z): 309.2 (M+H)+.

Example-24

Synthesis of Compound Number ARP100122, i.e., 3-(5-butylnicotinoyl)-1-methylpyrrolidin-2-one

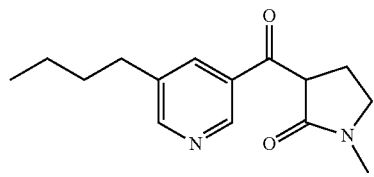 [SMILES: CCCCc1cncc(C(=O)C2CCN(C)C2=O)c1]

¹HNMR (500 MHz, CDCl3): δ ppm: 9.36 (s, 1H), 8.98 (s, 1H), 8.88 (s, 1H), 8.67 (s, 1H), 8.50-8.80 (m, 2H), 4.45 (q, 1H), 3.60 (m, 1H), 3.45 (m, 1H), 3.10 (m, 1H), 2.80-2.95 (m, 5H), 2.30 (m, 1H), 1.70 (m, 2H), 1.42 (m, 2H), 1.00 (t, 3H); Mass (m/z): 261.3 (M+H)+.

Example-25

Synthesis of Compound Number ARP100123, i.e., 3-(5-(3-hydroxyphenyl)nicotinoyl)-1-methylpyrrolidin-2-one

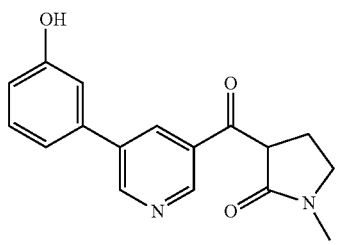

¹HNMR (500 MHz, CDCl3): δ ppm: 9.22 (s, 1H), 8.96 (s, 1H), 8.56 (s, 1H), 7.12-7.29 (m, 3H), 6.90 (d, 1H), 4.50 (q, 1H), 3.62 (m, 1H), 3.44 (m, 1H), 2.90 (s, 3H), 2.74 (m, 1H), 2.28 (m, 1H); Mass (m/z): 297.3 (M+H)+.

Example-26

Synthesis of Compound Number ARP100124, i.e., 3-(5-(2-chlorophenyl)nicotinoyl)-1-methylpyrrolidin-2-one

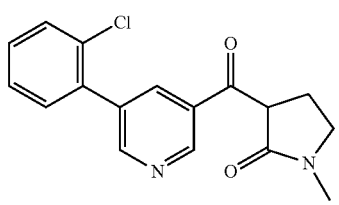

¹HNMR (500 MHz, CDCl3): δ ppm: 9.31 (s, 1H), 8.88 (s, 1H), 8.52 (s, 1H), 7.35-7.52 (m, 4H), 4.49 (q, 1H), 3.61 (m, 1H), 3.43 (m, 1H), 2.87 (s, 3H), 2.74 (m, 1H), 2.26 (m, 1H); Mass (m/z): 315.3 (M+H)+.

Example-27

Synthesis of Compound Number ARP100125, i.e., 3-(5-(3-aminophenyl)nicotinoyl)-1-methylpyrrolidin-2-one

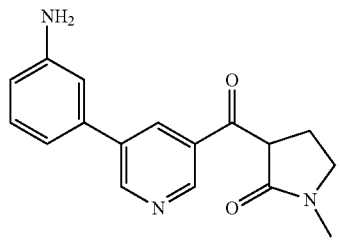

¹HNMR (500 MHz, CDCl3): δ ppm: 9.25 (s, 1H), 9.00 (s, 1H), 8.60 (s, 1H), 7.28 (m, 1H), 7.02 (d, 1H), 6.95 (s, 1H), 6.78 (d, 1H), 4.48 (q, 1H), 3.62 (m, 1H), 3.42 (m, 1H), 2.88 (s, 3H), 2.74 (m, 1H), 2.28 (m, 1H); Mass (m/z): 296.3 (M+H)+.

Correlation of Compound Numbers with Examples

| Example | Compound Number |
| --- | --- |
| 3 | ARP100101 |
| 4 | ARP100102 |
| 5 | ARP100103 |
| 6 | ARP100104 |
| 7 | ARP100105 |
| 8 | ARP100106 |
| 9 | ARP100107 |
| 10 | ARP100108 |
| 11 | ARP100109 |
| 12 | ARP100110 or APR10010 |
| 13 | ARP100111 |
| 14 | ARP100112 |
| 15 | ARP100113 |
| 16 | ARP100114 |
| 17 | ARP100115 |
| 18 | ARP100116 |
| 19 | ARP100117 |
| 20 | ARP100118 |
| 21 | ARP100119 |
| 22 | ARP100120 |
| 23 | ARP100121 |
| 24 | ARP100122 |
| 25 | ARP100123 |
| 26 | ARP100124 |
| 27 | ARP100125 |

Example 28

In addition to the other activities displayed, compounds of the invention variously exhibit anti-fungal and anti-bacterial activity, anti-amyloid plaque activity, anti-Parkinson's activity and low blood-brain barrier crossing effect, as measured by standard molecular docking techniques. The purpose of this example and Example 29 was to determine in vitro anti-microbial activity of the test molecules in Gram positive/Gram negative bacteria and fungi by the disc diffusion method.

The Kirby-Bauer disc diffusion method was used to determine the antimicrobial activity of test compounds. This is the most commonly used method for testing in vitro antimicrobial sensitivity.

Ciprofloxacin, Clindamycin, Amikacin, Flucanozole and Triclosan were used as standards. (Nictoine was used for comparative efficacy).

The bacterial cultures Gram positive bacteria (*Staphylococcus aureus, Enterococcus faecalis*), Gram negative bacteria (*E. Coli* and *Pseudomonas aeruginosa*) and fungal cultures (*Candida albicans* & *Cryptococcus neoformans*) were used.

a) Preparation of stock solutions of drugs/compounds. 5000 ug/ml stock solution was prepared in DMSO for each of the drugs. From this stock solution, other working stock solutions (100 ug/ml, 50 ug/ml, 25 ug/ml, 5 ug/ml) were prepared by serial dilution. All the working stock solutions were stored in a refrigerator up to two months. All the stock solutions were properly labeled.

b) Inoculum Preparation and Inoculation of Test Plates were done in accordance with well-known procedures.

c) Interpretation of Results. After incubation, each plate was examined for the zone of inhibition. The diameter of the zone of complete inhibition (as judged by the unaided eye) was measured in mm, including the diameter of the disc. The diameter of inhibition zone of different concentrations of the test compound was compared with the inhibition zones of reference standards in the usual manner.

d) Conclusion

Based on the results obtained in the above procedure, it was concluded that compounds ARP100105 and ARP100106 have both antibacterial and antifungal activity. ARP100105 showed activity at the concentrations of 100 µg and 50 µg and ARP100106 showed the activity at 100 µg. The compounds ARP100101 (100 µg and 50 µg), ARP100102 (100 µg, 50 µg, 25 µg, and 5 µg), ARP100104 (100 µg), ARP100108 (100 µg), ARP100119 (100 µg and 50 µg), ARP100120 (100 µg), ARP100121 (100 µg and 50 µg) and ARP100122 (100 µg) exhibit antifungal activity. ARP100111 showed antibacterial activity at 100 µg on both gram positive and gram negative bacteria. Nicotine did not show any antibacterial activity at 1000 µg/ml.

Example 29

Other antibacterial activity has been shown for various other compounds of the invention. Thus, this example shows the activity for compound ARP100115 and ARP100102 against *Mycobacterium Tuberculosis* and *Streptococcus mutans* respectively.

a) Anti-TB activity using Alamar Blue Dye.

1) The anti mycobacterial activity of compounds ARP100102 was assessed against *M. tuberculosis* (H37RV Strain) ATCC 25177, using microplate Alamar Blue assay (MABA) and compound to the reference drugs below.

2) This methodology is non-toxic, uses a thermally stable reagent and shows good correlation with BACTEC radiometric method.

3) Briefly, 200 µl of sterile deionized water was added to all outer perimeter wells of sterile 96 wells plate to minimized evaporation of medium in the test wells during incubation.

4) The 96 wells plate received 100 µl of the Middlebrook 7H9 broth and serial dilution of compounds were made directly on plate.

5) The final drug concentrations tested were 100 to 0.2 µg/ml.

6) Plates were covered and sealed with parafilm and incubated at 37° C. for five days.

7) After this time, 25 µl of freshly prepared 1:1 mixture of Almar Blue reagent and 10% tween 80 was added to the plate and incubated for 24 hours.

8) A blue color in the well was interpreted as no bacterial growth, and pink color was scored as growth.

9) The MIC was defined as lowest drug concentration which prevented the color change from blue to pink. Reference drugs minimum inhibition concentration:
Pyrazinamide—3.125 µg/ml
Steptomycin—6.25 µg/ml
Ciprofolxacin—3.125 µg/ml The test strain was sensitive to the test compound at levels down to 0.05 µg/ml, i.e. much lower than the MIC of the reference drugs shown above.

Reference: test employed was:

Evaluation of anti-Tubercular activity of nicotinic and isoniazid analogues. ARKIVOC 2007 (xv), 181-191.

Maria C. S. Lourenco, Marcus V. N deSouza, Alessandra C. Pinheiro, Marcelle de L. Ferreira, Rasnisb B, Goncalves, Thais Cristina M. Nogneira, Monica A. Peralta.

b) The purpose of this example was to determine the antibacterial activity of compound ARP100102 against *Streptococcus mutans* compared to reference drugs.

The Kirby Bauer procedure of Example 28 was followed except that the bacterial culture studied was *Streptococcus mutans* and the reference antibiotics were Ciprofloxacin, Clindamycin, Voncomyzin and Amikacin. When the diameter of the inhibition zone of the different concentration of the test compound was compared with the inhibition zones of the reference standard, the test results showed that Compound ARP100102 showed good antibacterial activity against *Streptococcus mutans* and *Corynebacterium* at 100 µg and 50 µg comparing favorably with the results obtained on the reference antibiotics at 5 µg to 30 µg concentration. The antibacterial activity of the compound was better on the *Streptococcus mutans* organism than on the *Corynebacterium* organism. *Streptococcus mutans* is the bacterium implicated in the formation of dental curies.

Example 30

Compounds ARP100102 and ARP100120 demonstrate analgesic activity as shown in the following tests.

A. The Acetic Acid-Induced Writhing Response test which causes abdominal constriction induced by intraperitoneal injection of acetic acid in the writhing test in mice was carried out according to the method of Koster et al. Male Albino Mice were divided into the following groups of six animals each as follows:

Experiment:

1. Group-I: Control-Normal saline (0.1 ml i.p./10 gm)
2. Group-II: Diclofenac (10 mg/kg body weight, i.p.)
3. Group-V: Compound-ARP100120 (3 mg/kg body weight, i.p.)

The number of writhes (abdominal muscular contractions), stretching of the hind limbs and trunk twisting were counted 5 minutes after the injection of 1% acetic acid (v/v, 0.1 mL/10 g body weight, i.p.). The data collected represented the total number of writhes observed in duration of 10 minutes (5-15 minutes after the injection). Percentage inhibition was then calculated. Percentage inhibition =(N−N$^t$/N)×100, where N is the average number of writhing of control group and N$^t$ is the average number of writhing of test group.

Results are as follows:

| Groups | Number of Writhing | Percentage Inhibition |
| --- | --- | --- |
| Control | 47.17 ± 4.167 | None |
| Diclofenac | 34.50 ± 1.586* | 26.86 |
| ARP100 | 30.67 ± 1.706*** | 34.94 |

As can be seen, maximum writhing inhibition occurred with the test compound thus suggesting its use as a peripheral analgesic on a par with the standard drug diclofenac.

B. The Eddy Hot Plate method was used to evaluate the CNS analgesic effect of the test compound. Male Wistar rats initially weighing 180-200 g were divided into the following groups of six animals each as follows:

Experiment-I:
1. Group-I: Control—10% Dimethyl sulfoxide (DMSO) (0.5 ml s.c)
2. Group-II: Standard—Pentazocine (20 mg/kg body weight, s.c.)
3. Group-III: Compound-ARP100102 (0.5 mg/kg body weight, s.c.)

Experiment-II:
Same as Experiment I except Group III dosage was 1 mg/kg body weight.

The hot plate method was originally developed by Woolfe and MacDonald (1944). The paws of rat are very sensitive to heat at temperatures which are not damaging to the skin. The response is in the form of jumping, withdrawal of paws or licking of the paws (Eddy and Leimback, 1953). The animals were placed on Eddy's hot plate at a temperature of 55±0.5° C. A cut off period of 20 s, was observed to avoid damage to the paw. Reaction time and the type of response were noted using a stopwatch. The latency was recorded before and after 30, 60, 90 and 120 minutes following s.c. injection of test compounds (0.5 mg and 1 mg·kg), standard drug (pentazocine) and control vehicle respectively. The dose selection of the test compounds was based on the literature of nicotine (0.32-1.6 mg/kg s.c.). Average reaction time was then calculated and the percentage variation calculated using the following ratio:

Percentage protection=Drug latency−Baseline latency×100Baseline latency

The results obtained from the experiments reveal that the test compound ARP100 showed significant analgesic activity as compared to the standard drug by significantly increasing the reaction time in the hot plate test, suggesting its potential as a central nervous system analgesic.

Eddy NB, Leimbach DJ. J Pharmacol Exptl Therap 1953; 107; 385.

Example 31

Molecular Docking Studies

Compounds of the invention were evaluated in docking studies to evaluate the correlation between the compounds and an art-recognized receptor for a given disease or condition as shown below.

Molecular docking studies are a well-known device for determining the ability of a compound under study to react or "dock" with a receptor site well-known to be responsible for various conditions or diseases of interest.

Conformation of the compound under evaluation with the receptor site as measured by the ability of the compound to "dock" with the site, and the extent to which it does so, is a measure of the activity of the compound to alter the biological function of the receptor site.

The following known receptors of the indicated conditions were used in the conformational studies of this Example:
For Alzheimer's Disease:
  Receptor A—acetyl cholinesterase
  Receptor B—N-methyl-D-aspartate (NMDA)
  Receptor C—Butyrylcholinesterase
  Receptor E—Beta Secretes for anti-amyloidal activity
  Receptor F—molluscan acetylcholine-binding protein (ACHBP)
For Alzheimer's Disease, Schizophrenia, Parkinson's Disease, Depression, ADHD and Tobacco addiction:
  Receptor G—alpha 7 nicotinic acetylcholine receptor (alpha7nAhR) for memory
For Serotonin: 5HT4 Receptor
For Parkinson's Disease:
  Receptor D—Metabotropic Glutamate receptor type 4 (mGluR4)
For Chantix-Like anti-nicotine activity (reduction of nicotine craving)
  Receptor H—10ED
  Receptor I—10 LE
  Receptor J—2BG9
  Receptor K—3SQ9
  Receptor L—IUX2

Using the foregoing known receptors in docking studies carried out in accordance with techniques well-known in the art, activity of the compounds shown below against the relevant condition, was indicated by the low docking scores of the compounds of the invention compared to the docking score of the nicotine control.
  Alzheimer's Disease: Compounds ARP100101, ARP100107, ARP100108, ARP100110, ARP100112, ARP100113, ARP100116, ARP100117, ARP100119, ARP100120, ARP100123 and ARP100125
  Parkinson's Disease—ARP100101, ARP100107, ARP100110, ARP100112, ARP100116, ARP100117, ARP100119, ARP100125
  Schizophrenia—ARP100110
  Antidepressant—ARP100101
  ADHD—ARP100110
  Chantix Like—ARP100112, ARP100114, ARP100116 and ARP100123

While the invention has been described in detail and with reference to specific examples thereof, it will be apparent to one skilled in the art that various changes in modifications can be made therein without departing from the spirit and scope thereof.

What is claimed is:

1. The method for treating a microbial or fungal infection which comprises administering to a host suffering from such infection an antimicrobially or antifungally effective amount of a compound of formula (I),

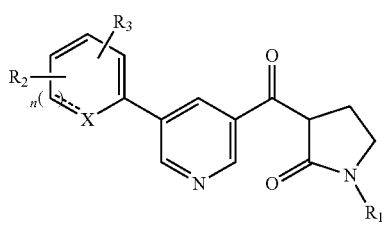

wherein:
X is CH, N or S;
n is 0 or 1;
R₁ is hydrogen, acyl, alkyl, halogen, alkoxy, aldehyde, hydroxy, cyano, nitro, amino, aryl, heteroaryl or heterocyclyl;
R₂ is hydrogen, acyl, alkyl, halogen, alkoxy, aldehyde, hydroxy, cyano, nitro, amino, aryl, heteroaryl or heterocyclyl; or salt thereof;
R₃ is hydrogen, acyl, alkyl, halogen, alkoxy, aldehyde, hydroxy, cyano, nitro, amino, aryl, heteroaryl or heterocyclyl and wherein
R₂ and R₃ may be joined together to form a cycylic ring such as aryl, heteroaryl or heterocyclic.

2. The method of claim 1, wherein the compound is selected from the group consisting of:
3-(5-(5-acetylthiophen-2-yl)nicotinoyl)-1-methylpyrrolidin-2-one;
3-(5-(4-fluorophenyl)nicotinoyl)-1-methylpyrrolidin-2-one;
3-(5-(1-methyl-2-oxopyrrolidine-3-carbonyl)pyridin-3-yl)benzaldehyde;
1-methyl-3-(5-m-tolylnicotinoyl)pyrrolidin-2-one;
3-(5-(4-chlorophenyl)nicotinoyl)-1-methylpyrrolidin-2-one;
4-(5-(1-methyl-2-oxopyrrolidine-3-carbonyl)pyridin-3-yl)benzaldehyde;
3-(5-(3-methoxyphenyl)nicotinoyl)-1-methylpyrrolidin-2-one;
3-(5-(4-methoxyphenyl)nicotinoyl)-1-methylpyrrolidin-2-one;
1-methyl-3-(5-p-tolylnicotinoyl)pyrrolidin-2-one;
1-methyl-3-(5-phenylnicotinoyl)pyrrolidin-2-one;
3-(5-(3-fluorophenyl)nicotinoyl)-1-methylpyrrolidin-2-one;
1-methyl-3-(5-(3-nitrophenyl)nicotinoyl)pyrrolidin-2-one;
3-(5-(2-methoxyphenyl)nicotinoyl)-1-methylpyrrolidin-2-one;
1-methyl-3-(5-o-tolylnicotinoyl)pyrrolidin-2-one;
3-(5-(3,5-dichlorophenyl)nicotinoyl)-1-methylpyrrolidin-2-one;
1-methyl-3-(5-(naphthalen-1-yl)nicotinoyl)pyrrolidin-2-one;
3-(5-(3-acetylphenyl)nicotinoyl)-1-methylpyrrolidin-2-one;
3-(5-cyclopropylnicotinoyl)-1-methylpyrrolidin-2-one;
1-methyl-3-(5-(naphthalen-2-yl)nicotinoyl)pyrrolidin-2-one;
4-(5-(1-methyl-2-oxopyrrolidine-3-carbonyl)pyridin-3-yl)phenyl acetate;
3-(5-(1-methyl-2-oxopyrrolidine-3-carbonyl)pyridin-3-yl)benzaldehyde;
3-(5-(3-hydroxyphenyl)nicotinoyl)-1-methylpyrrolidin-2-one;
3-(5-(2-chlorophenyl)nicotinoyl)-1-methylpyrrolidin-2-one; and
3-(5-(3-aminophenyl)nicotinoyl)-1-methylpyrrolidin-2-one.

3. The method according to claim 1 wherein the infection is a *Mycobacterium tuberculosis* infection and the compound administered comprises:
3-(5-(3,5-dichlorophenyl)nicotinoyl)-1-methylpyrrolidin-2-one.

4. The method according to claim 1 wherein the infection is a *Streptococcus mutans* infection and the compound administered is 3-(5-(4-fluorophenyl)nicotinoyl)-1-methylpyrrolidin-2-one.

5. The method for alleviating pain in a subject which comprises administering to a host suffering from pain, a pain-relieving amount of a compound selected from the group consisting of:
4-(5-(1-methyl-2-oxo-pyrrolidin-3-carbonyl)pyridine-3 yl)phenylacetate and 3-(5-(4-fluorophenyl)nicotinoyl)-1-methylpyrrolidin-2-one.

* * * * *